United States Patent
Holte et al.

(12)

(10) Patent No.: US 6,216,023 B1
(45) Date of Patent: Apr. 10, 2001

(54) METHOD AND APPARATUS FOR DETERMINING DIFFERENCES BETWEEN REGIONAL $CO_2$ AND SYSTEMIC $CO_2$ MEASUREMENTS

(75) Inventors: Bo Holte, Charlottenlund (DK); Michael Mythen, London (GB)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/218,876

(22) Filed: Dec. 22, 1998

(51) Int. Cl.$^7$ .................................................. A61B 5/00
(52) U.S. Cl. .......................... 600/345; 600/309; 600/347; 600/353; 600/364
(58) Field of Search ................................... 600/345–365, 600/375, 397

(56) References Cited

U.S. PATENT DOCUMENTS 6,029,076 * 2/2000 Fiddian-Greene et al. .......... 600/353

FOREIGN PATENT DOCUMENTS

| 122952 | 10/1984 | (EP) . |
| 251931 | 1/1988 | (EP) . |
| 94/21163 | 9/1994 | (WO) . |

OTHER PUBLICATIONS

*The role of gut mucosal hypoperfusion in the pathogenesis of post–operative organ dysfunction*, M. G. Mythen, A. R. Webb, Intensive Care Medicine (1994) 20:203–209.
*Gastric Intramucosal pH: A noninvasive Method for the Indirect measurement of Tissue Oxygenation*, Cinda H. Clark, RN, BSN, and Guillermo Gutierrez, MD, PhD, American Journal of Critical Care, vol. 1, No. 2, (1992) 2:53–60.
*The Arterial to End–Tidal Carbon Dioxide Gradient increases with Uncorrected but Not with Temperature–corrected $Paco_2$ Determination during Mild to Moderate Hypothermia*, Christian Sitzwohl, MD, et al. Anesth. Analg. (1998) 86:1131–6.

* cited by examiner

Primary Examiner—Cary O'Connor
Assistant Examiner—Michael Astorino
(74) Attorney, Agent, or Firm—Andrus, Sceales, Starke & Sawall, LLP

(57) ABSTRACT

Methods and apparatus for determining the difference between a regional $CO_2$ partial pressure of a selected body organ of a mammalian subject, such as the gut, and a systemic $CO_2$ partial pressure of the subject. The regional $CO_2$ partial pressure value is tonometrically obtained at body temperature using a gaseous sampling medium. A systemic $CO_2$ partial pressure value is obtained from the blood. The systemic $CO_2$ partial pressure value can be that for the body temperature or for a standard temperature. If the systemic $CO_2$ partial pressure value is that for the body temperature, the regional $CO_2$ partial pressure value is compared to the systemic $CO_2$ partial pressure value and the difference therebetween is provided as a $CO_2$ partial pressure gap measurement. If the systemic $CO_2$ partial pressure value is that for a standard temperature, one of the regional $CO_2$ partial pressure value or the systemic $CO_2$ partial pressure value is corrected for the difference between the body temperature and the standard temperature so that both the partial pressure values comprise $CO_2$ partial pressure values at a common temperature. The values are thereafter compared to provide a $CO_2$ partial pressure gap measurement. An end tidal $CO_2$ partial pressure value may be used as the systemic $CO_2$ partial pressure value.

25 Claims, 4 Drawing Sheets

METHOD AND APPARATUS FOR DETERMINING DIFFERENCES BETWEEN REGIONAL $CO_2$ AND SYSTEMIC $CO_2$ MEASUREMENTS

BACKGROUND OF THE INVENTION

The present invention relates to improved methods and apparatus for determining differences between $CO_2$ levels in a specific organ or region of the body of a mammalian subject and systemic $CO_2$ levels in the blood of the subject.

Regional $CO_2$ measurements are typically obtained from the mucosa or other tissue found in an organ or region of the body, for example, the gastrointestinal tract or urinary bladder. One way of obtaining such measurements is to place a tonometric catheter having a sampling chamber permeable to $CO_2$ in a hollow organ of the body, such as the stomach or intestine, so that the sampling chamber is contiguous with the mucosa of the gut. A fluid sampling medium is supplied to the sampling chamber through a tube. The sampling medium receives $CO_2$ which passes from the mucosa into the sampling chamber. The sampling medium is then removed from the chamber through the tube and the regional $CO_2$ level is measured by suitable gas analysis means. See for example published PCT application PCT/US94/02953 and corresponding U.S. national stage application Ser. No. 08/433,398, filed May 18, 1995 describing catheters of this type and their uses. The measurement is typically expressed as a regional $CO_2$ partial pressure ($PrCO_2$).

Regional tonometric measurements provide an indication of the condition of the organ. It is becoming more fully appreciated that tonometric measurements, such as gastrointestinal measurements, can be used to provide an early indication or warning of serious physiological conditions which may be difficult to otherwise diagnose. Such conditions include dysoxia (deficiency in oxygen delivery), hypovolemia (abnormally decreased volume of circulating fluid in body), sepsis, and shock. The early indication arises from the fact that the gastrointestinal tract is the first organ of the body to be affected by such a condition as reflected in reduced mucosal perfusion (blood flow) in the gastrointestinal tract. The reduced perfusion in turn, increases the regional $CO_2$ partial pressure. Since the altered $CO_2$ partial pressure can be ascertained tonometrically, tonometric monitoring is particularly valuable in surgical recovery units, intensive care units, and other settings. See for example, "The Role of Gut Mucosal Hyperfusion in the Pathogenesis of Post-operative Organ Dysfunction" by M. G. Mythen and A. R. Webb, Intensive Care Medicine (1994), 20:203–209 and "Gastric Intramucosal pH: A Non-invasive Measurement for the Indirect Measurement of Tissue Oxygenation" by Cinda H. Clark and Guillermo Gutierrez in American Journal of Critical Care (1992), 2:53–60.

A convenient and straightforward indication of the state of gut mucosal perfusion is the difference between a regional $CO_2$ partial pressure measurement ($PrCO_2$) obtained tonometrically from the organ and the systemic $CO_2$ partial pressure, for example, that existing in arterial blood ($PaCO_2$). See the PCT patent application and the Mythen et al. article, supra. Venous blood $CO_2$ partial pressure ($PvCO_2$) can also be used. An increase in the $CO_2$ partial pressure difference, or the "$CO_2$ gap", between the regional and systemic $CO_2$ levels indicates a reduction in the adequacy of gut mucosal perfusion and the onset of dysoxia and/or other conditions hazardous to the patient.

The $CO_2$ level of arterial blood is typically measured by periodically drawing a blood sample from the patient into a cuvette. The cuvette is then carried to, and placed in, a blood gas analyzer that uses, for example, electrochemical sensors, to measure the partial pressure of the sample. Or, a probe may be placed in an artery of the patient to obtain blood samples.

Because electrochemical sensors are temperature sensitive and because the temperature of the blood sample will change during transport to the blood gas analyzer, it has become conventional to correct blood $CO_2$ partial pressure measurements to a standard temperature. Also, the blood $CO_2$ partial pressure will vary with the temperature of the subject. For example, if the body temperature of the subject is reduced from the usual body temperature, a decrease in the partial pressure $PaCO_2$ will occur, for a given amount of $CO_2$ in the blood.

The use of a standard temperature permits data periodically obtained from a patient to be meaningfully compared even though the temperature of the patient changes in the course of time or permits data from a given patient to be compared to data obtained from other patients or compared to recognized criteria. Standard temperature arterial $CO_2$ partial pressure values avoid confusion, as when a patient is attended by a number of physicians. For the foregoing reasons, use of standard temperature blood $CO_2$ partial pressure values has become an accepted medical protocol. The standard temperature is typically 37° (98.6° F.), the normal temperature of the human body. The blood gas analyzer contains thermal control apparatus to ensure that the blood sample is at the standard temperature when the measurement of $PaCO_2$ is made and contains a correction algorithm to correct the measurement to the actual temperature.

Recently, the use of gas as the tonometric sampling medium has come into use. Air may be used for this purpose. A gas analysis means, such as an infrared spectrometer, is connected directly to the tonometric catheter. The gaseous sampling medium is withdrawn from the sampling chamber of the tonometric catheter and passed through the gas analysis means, such as an infrared spectrometer, connected to the catheter to determine the regional $CO_2$ partial pressure. The sampling medium withdrawn from the tonometer is at the existing actual temperature of the organ, which is usually the body temperature of the subject, and the regional $CO_2$ partial pressure determination is thus made at that temperature.

The tonometrically obtained regional $CO_2$ partial pressure ($PrCO_2$) is compared to the arterial $CO_2$ partial pressure ($PaCO_2$) to determine the $CO_2$ gap. This is currently done notwithstanding the fact that the regional $CO_2$ partial pressure is an actual body temperature value whereas the arterial $CO_2$ partial pressure is a standard temperature value. This use of values obtained for two different temperatures introduces the possibility of error in the determination of the $CO_2$ gap.

For a normal person, the standard and actual body temperatures are the same (both 37° C.) so that any errors are small or non-existent. But, actual body temperatures vary, and can vary over a wider range than is often appreciated. Fevers increase the actual body temperature above 37° C., for example to 40° C. (104° F.). In many medical procedures, the temperature of a patient is deliberately reduced to slow metabolic functions, reduce swelling, or for other reasons. Reductions to a temperature of 30° C. (86° F.) may occur. Greater differences between actual body temperature of the subject and the standard temperature correspondingly increase the error in the determination of the regional-arterial $CO_2$ partial pressure gap. These errors may result in inappropriate diagnosis and/or treatment of the subject.

The invasive and intermittent nature of obtaining direct arterial $CO_2$ partial pressure measurements by periodically drawing blood or using probes has led to determining systemic $CO_2$ levels non-invasively and continuously by using the exhaled respiration gases of the patient. Typically, the $CO_2$ level existing at the end of exhalation, the end-tidal level ($EtCO_2$), is used for this purpose. The end-tidal determination is carried out at actual body temperature.

In normal persons, the use of end tidal $CO_2$ measurements in lieu of arterial blood $CO_2$ measurements is usually appropriate since the gradient between the two is low and constant so that it is possible to determine the $CO_2$ gap by a comparison of $PrCO_2$ and $PetCO_2$. However, for many persons, or for subjects in particular circumstances, such as mechanically ventilated patients, the correlation between $PetCO_2$ and $PaCO_2$ is lower. Further, unless the standard temperature $PaCO_2$ value is compensated for the actual temperature of the subject, the gradient between $PetCO_2$ and $PaCO_2$ will change as the temperature of the subject changes. See "The Arterial to End-Tidal Carbon Dioxide Gradient Increases with Uncorrected $PaCO_2$ Determination During Mild to Moderate Hypothermia", Christian Sitzwohl et al., Anesthesia Analc 1998; 86.

Concern over the use of end tidal $CO_2$ for the foregoing reasons and/or a preference for a particular blood gas analysis protocol has lead some medical practitioners to prefer standard temperature blood gas analysis $CO_2$ values, while others use actual temperature blood gas analysis values, while others use end-tidal $CO_2$ values. This has, correspondingly, made obtaining $CO_2$ gap measurements that are understood by, and acceptable to, medical practitioners difficult and has detracted from full realization of the usefulness of such measurements.

BRIEF SUMMARY OF THE INVENTION

It is, therefore, the object of the present invention to provide methods and apparatus for providing an improved regional-systemic $CO_2$ partial pressure gap measurement for use in diagnostic, treatment or other purposes.

More particularly, it is an object of the present invention to provide methods and apparatus for providing an accurate indication of the regional-artetial $CO_2$ partial pressure gap and in which errors arising from the use of values reflecting $CO_2$ partial pressures obtained at different temperatures are eliminated.

A further object of the present invention is to provide such methods and apparatus which permit the use of end tidal $CO_2$ partial pressures to determine the $CO_2$ gap.

Various other features, objects, and advantages of the invention will be made apparent from the following detailed description and the drawings.

DETAILED DESCRIPTION OF THE INVENTION

Figure 1:
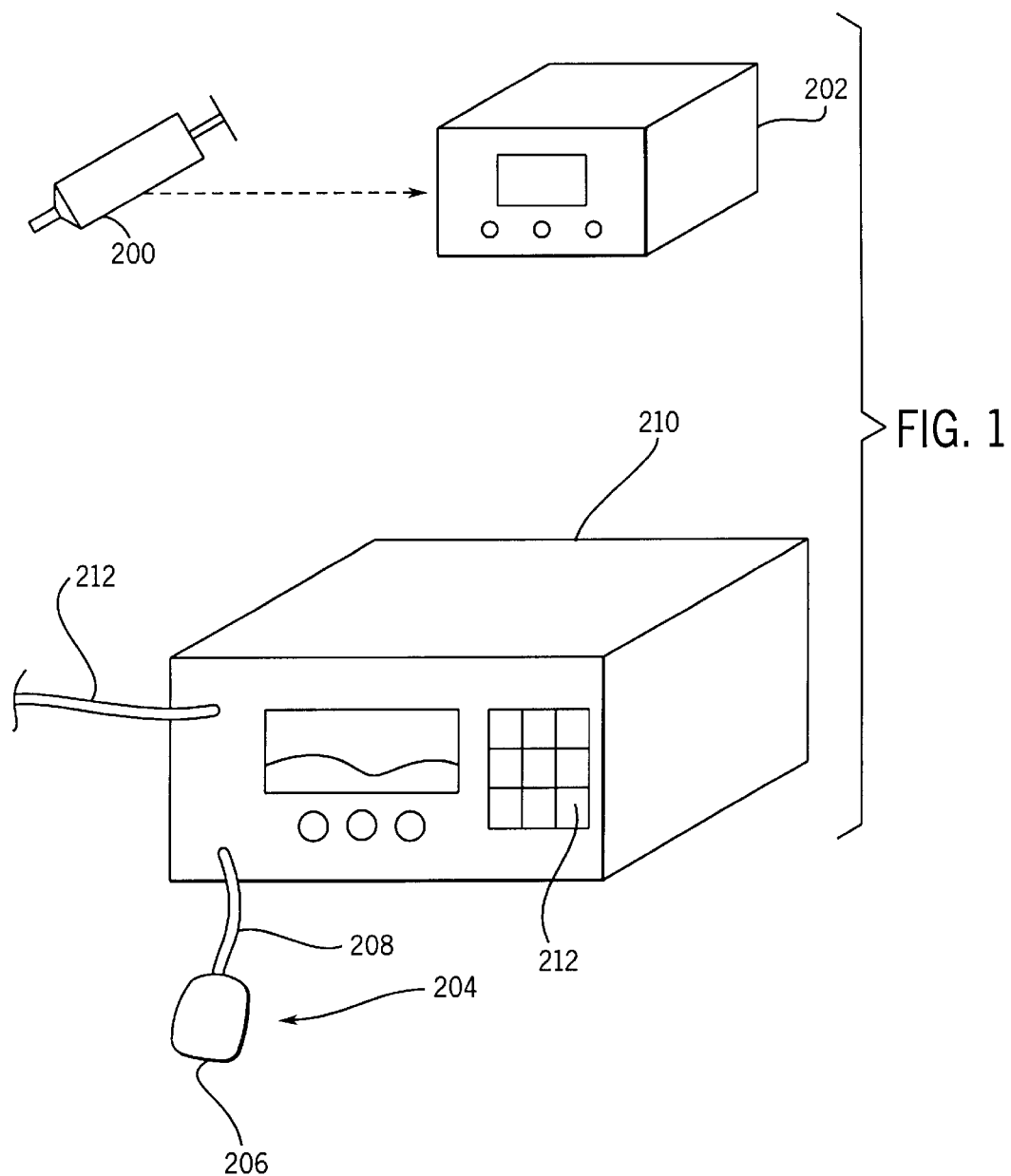
FIG. 1 is a simplified showing of the apparatus of the present invention which may be utilized to carry out the method of the present invention.
Figure 2:
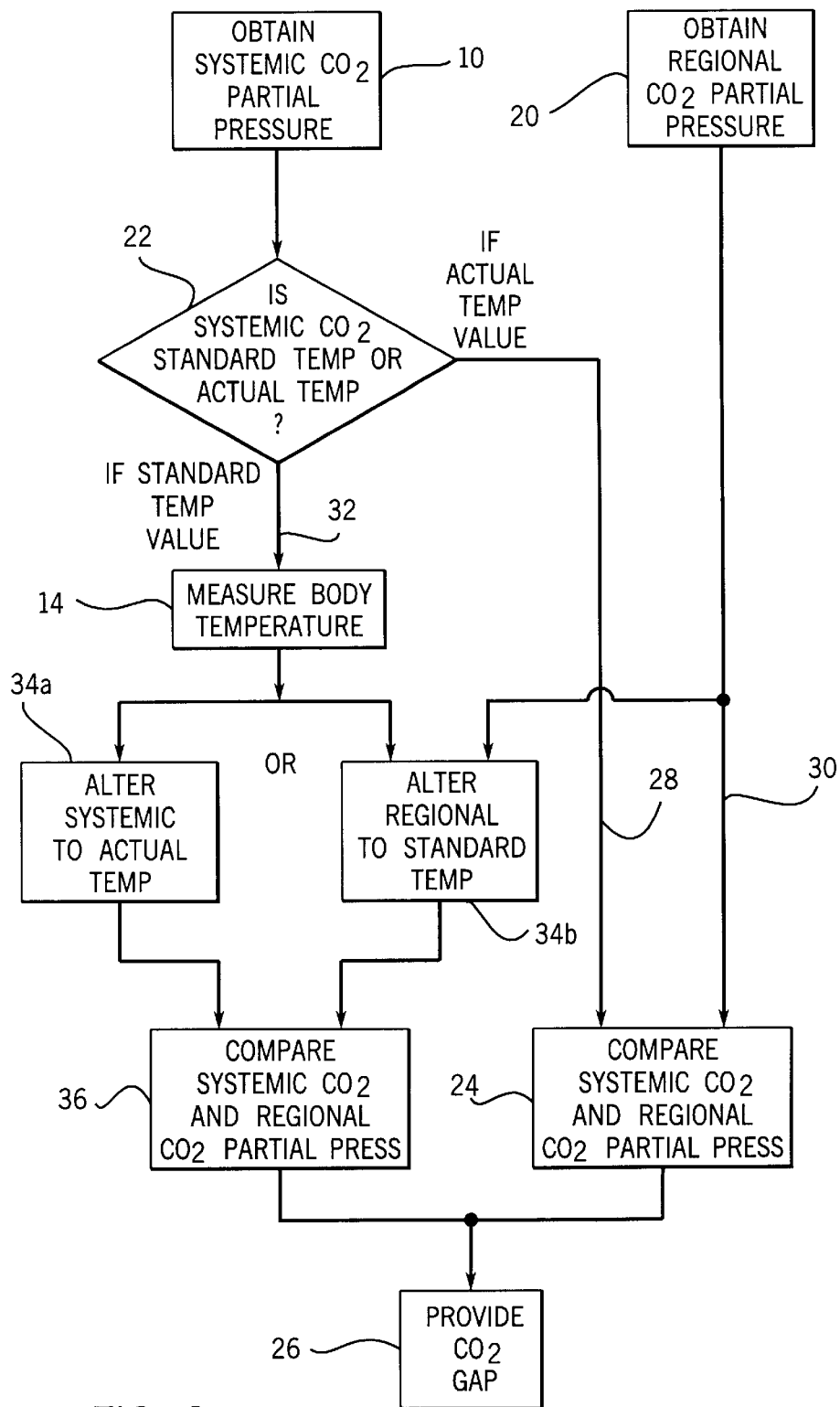
FIG. 2 is a simplified block diagram showing the steps of the method of the present invention.

In the method and apparatus of the present invention, it is necessary to obtain a systemic $CO_2$ partial pressure value as shown in step 10 in FIG. 2. To this end, a sample of arterial blood is withdrawn from the subject, for example through an arterial catheter into a preheparinized syringe 200 shown in FIG. 1. See step 11 in FIG. 3. The barrel of the syringe may be used as a cuvette or the sample may be transferred to a separate cuvette. The cuvette is then transported to and placed in conventional blood gas analysis equipment 202 where the arterial $CO_2$ partial pressure ($PaCO_2$) is determined, as by using electrochemical electrodes. In accordance with conventional practice, the blood gas analysis equipment 202 typically employs temperature control apparatus to establish and maintain the blood sample being analyzed at a standard temperature so as to provide a standard temperature arterial $CO_2$ partial pressure value at step 12. Under current medical protocols, the standard temperature is 37° C.

Or, if the blood sample is not at the standard temperature, the blood gas analyzer may carry out a computational temperature correction to provide a standard temperature value. For this purpose, the temperature of the sample is determined. The output of the blood gas analyzer is corrected in accordance with the temperature differences at step 13 to provide a blood $CO_2$ partial pressure measurement ($PaCO_2$) at the standard temperature.

With some blood gas analyzers currently in use the actual body temperature of the subject, as measured in step 14 can be entered to provide a reading of blood $CO_2$ partial pressure ($PaCO_2$) comprising that for the actual body temperature. See step 15.

To obtain the regional $CO_2$ partial pressure in step 20, a tonometric catheter 204 is placed in or adjacent the organ of interest. As noted above, such a catheter has a hollow sampling chamber 206 that is permeable to $CO_2$. A tube 208 extends from the chamber to outside the body of the patient. The distal end of the tube is connected to a sampling chamber. The proximal end of the tube is connected to the gas input connection of apparatus for measuring $CO_2$ levels in gaseous media. Such apparatus is typically capnograph 210. The capnograph made and sold by the Datex-Ohmeda division of Instrumentarium Corp., Helsinki, Finland under the trademark "Tonocap" can be used as capnograph 210. Capnograph 210 contains microprocessor or other circuitry suitable for carrying out steps of the present invention. Means, such as a pump, are provided in capnograph 210 to inflate the sampling chamber with a gaseous sampling medium, such as air, through tube 208. The sampling medium receives $CO_2$ passing from the organ into the sampling chamber. After a period of time sufficient to allow the level of $CO_2$ in the sampling medium to equilibrate with the $CO_2$ level in the organ of interest, the pump is operated to draw the gaseous sampling medium out of sampling chamber 206 into capnograph 210 where the gaseous sampling medium containing the $CO_2$ is analyzed, typically by an infrared spectrometer, to determine the concentration of $CO_2$ in the sampling medium. The value so determined is corrected for ambient atmospheric pressure to arrive at a regional $CO_2$ partial pressure ($PrCO_2$). The sampling cycle is then usually repeated at preset intervals.

It will be appreciated that since sampling chamber 206 of tonometric catheter 204 is in or adjacent to the organ of interest, the measurement of regional $CO_2$ partial pressure value ($PrCO_2$) will be that for the actual temperature of the organ.

A capnograph 210 suitable for use in the present invention allows entry of a systemic $CO_2$ partial pressure value, for example, the arterial blood ($PaCO_2$) value obtained from the blood gas analyzer, as at key pad 212. The operator also inserts an indication of whether the systemic $CO_2$ partial pressure from step 10 is that for the standard temperature or in that for the actual body temperature of the subject. See step 22.

If the systemic $CO_2$ partial pressure value is that for the actual body temperature of the subject, this partial pressure value is compared directly with the regional $CO_2$ partial pressure ($PrCO_2$) value at step 24. The $CO_2$ "gap" difference or measurement obtained from the comparison is provided at step 26. In FIG. 2, the step paths 28 and 30 lead to value comparison step 24.

If, as is often the case, the systemic $CO_2$ partial pressure, for example, an arterial value, is that for the standard temperature, the step path becomes that indicated by 32. The actual temperature of the subject, measured at step 14, is inputted into capnograph 210. A correction is then carried out at step 34a or 34b to alter one of the systemic $CO_2$ partial pressure ($PaCO_2$) (step 34a) or the regional $CO_2$ partial pressure ($PrCO_2$) (step 34b) so that both $CO_2$ partial pressure values are those representative of $CO_2$ partial pressures at a common temperature.

For example, if it is desired to correct a standard temperature arterial $CO_2$ partial pressure value ($PaCO_2$) to that of the actual temperature of the subject as in step 34a, an algorithm suitable for this purpose is $PCO_2(T) = PCO_2(37°) \times 10^{0.019 \times (T-37)}$ where T in the exponent is the actual temperature of the subject. A corresponding algorithm may be derived if it desired to correct the actual body temperature regional $CO_2$ partial pressure to a standard temperature value in alternative step 34b. In carrying out the present invention, it is presently seen as preferred to correct the actual body temperature regional $CO_2$ partial pressure at step 34b to a standard temperature value.

With one of the systemic $CO_2$ value or $PrCO_2$ value corrected so that both values represent $CO_2$ partial pressures at a common temperature, i.e. the standard temperature or the actual body temperature, the systemic $CO_2$ partial pressure, as represented by the $PaCO_2$ value, and the regional $CO_2$ partial pressure $PrCO_2$ are compared at step 36 to produce the difference comprising the $CO_2$ gap at step 26. The use of common temperature $CO_2$ partial pressure values insures that the resulting $CO_2$ gap determination is an accurate, medically useful measurement.

Figure 4:
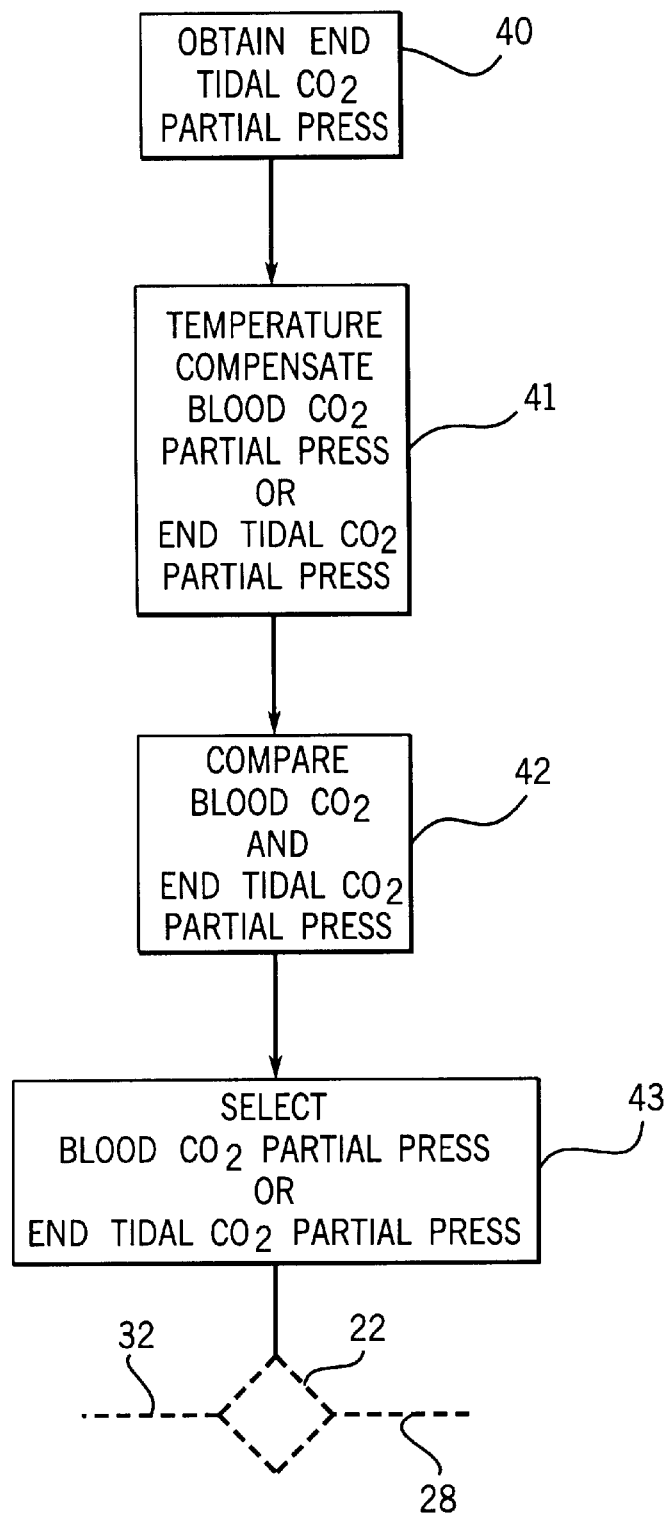
FIG. 4 is a block diagram showing the steps in an embodiment of the method of the present invention in which an end tidal $CO_2$ partial pressure value is employed.

FIG. 4 shows the steps of a method in which the end tidal $CO_2$ partial pressure value ($PetCO_2$) is also obtained, as at step 40. As noted above, use of end tidal $CO_2$ values as an indication of systemic $CO_2$ partial pressures is advantageous in that it is non-invasive and continuous but may not always accurately indicate the actual systemic $CO_2$ partial pressure, as reflected in the arterial blood ($PaCO_2$). To obtain the end-tidal $CO_2$ partial pressure value, a breathing mask or endotracheal tube is provided for the subject and connected via a breathing circuit to a mechanical ventilator. A side stream sample of the breathing gases can be removed from the breathing circuit in conduit 212 and supplied to capnograph 210 for determination of the end tidal $CO_2$ partial pressure ($PetCO_2$) value. Or a main-stream sensor may be placed in the breathing circuit for determining the end tidal $CO_2$ partial pressure value ($PetCO_2$), and for providing a signal corresponding to same to capnograph 210. The end tidal $CO_2$ partial pressure value will be that for the temperature of the lungs of the subject. This will normally be the same as the temperature of the organ containing the tonometric catheter due to the uniform body temperature produced by homeostasis that characterizes mammalian subjects.

In the method of FIG. 4, in the event that the arterial $CO_2$ partial pressure value is that corresponding to standard temperature, the correction carried out in step 41, to reflect the actual temperature of the subject is either to correct the standard temperature value of the blood partial pressure value ($PaCO_2$) to an actual temperature value or to correct the end tidal $CO_2$ partial pressure value to standard temperature value. Thus, the $PetCO_2$ value can be changed to a standard temperature value or the $PaCO_2$ value can be changed to an actual body temperature value.

In the method of FIG. 4, it is then necessary to determine whether or not end tidal $CO_2$ partial pressure values can be used as the indication of systemic blood $CO_2$ partial pressure values for determining the $CO_2$ gap. To this end, in step 42, it is necessary to compare the blood $CO_2$ partial pressure value ($PaCO_2$) and the end tidal $CO_2$ partial pressure value ($PetCO_2$) that are now on a same-temperature basis. If there is a high correlation between the two values, that is, if there is a small difference between the two, it is preferable to use end tidal $CO_2$ values for the reasons given above. If there is not a high correlation, or if other circumstances require, the arterial $CO_2$ partial pressure value obtained from blood gas analyzer 102 may be employed. The appropriate one of blood $CO_2$ partial pressure value or the end tidal $CO_2$ partial pressure value is then selected at step 43 for use as the systemic $CO_2$ partial pressure value in the remaining steps of the method shown in FIG. 2.

Figure 3:
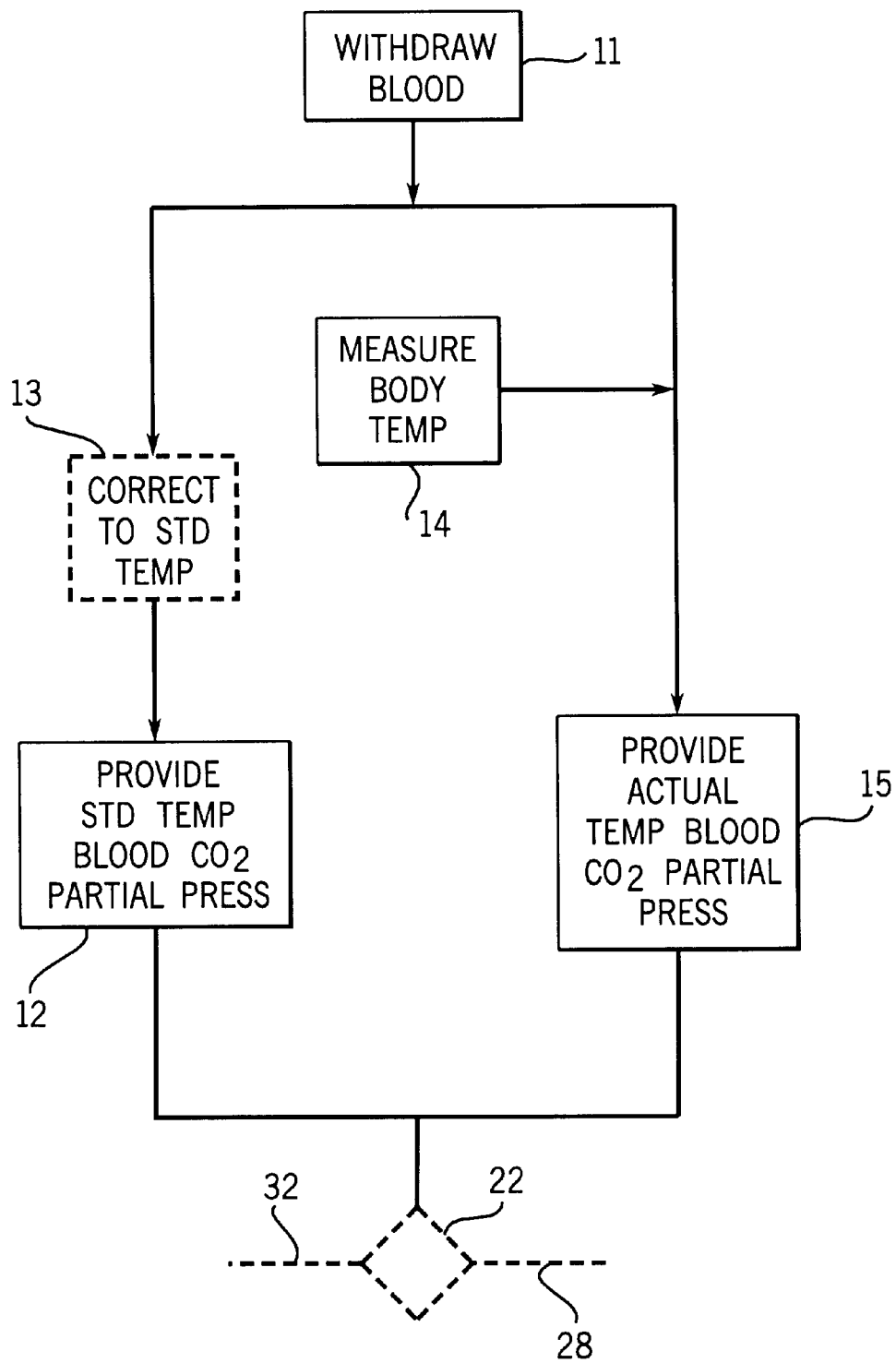
FIG. 3 is a block diagram showing further details of the method shown in FIG. 2.

The above description includes the correction of either blood $CO_2$ partial pressure and/or regional $CO_2$ partial pressure ($PrCO_2$), as in the method of FIGS. 2 and 3, or additional correction of end-tidal $CO_2$ value, as in the embodiment shown in FIG. 4, so that the comparison of steps 24 and 36 are made on a same temperature basis. However, with the appropriate algorithm, it could also be possible to obtain the $CO_2$ gap at step 26 and if the systemic $CO_2$ partial pressure value obtained from the blood sample or end tidal respiration and the regional $CO_2$ partial pressure value are not same temperature values, to modify the $CO_2$ partial pressure gap value in accordance with the temperature difference between the standard temperature and the actual body temperature of the subject to provide an accurate indication of the $CO_2$ gap.

Also, while the present invention has been described in connection with the measurement of $CO_2$ partial pressures, it will be appreciate that it may be used in connection with other gases of interest, such as oxygen. And, while the use of arterial $CO_2$ partial pressures have been described, as noted in the introduction portion of this specification, it is also possible to use venous $CO_2$ partial pressures.

It is recognized that other equivalents, alternatives, and modifications aside from those expressly stated, are possible and within the scope of the appended claims.

What is claimed is:

1. A method for determining the difference between a regional gaseous partial pressure of a selected body organ of a mammalian subject and a systemic gaseous partial pressure of the subject, the body temperature of the subject being changeable, said method comprising the steps of:

(A) tonometrically obtaining a regional gaseous partial pressure value from the selected body organ of the subject using a gaseous sampling medium, the regional partial pressure value being that for the body temperature of the subject;

(B) obtaining a systemic gaseous partial pressure value from the blood of the subject;

(C) ascertaining whether the systemic partial pressure value of the subject is that for a standard temperature or that for the body temperature of the subject;

(D) if the systemic partial pressure value is that for the body temperature of the subject, (E) comparing the regional partial pressure value to the systemic partial pressure value and providing the difference therebetween as a partial pressure gap measurement;

(F) if the systemic partial pressure value is that of a standard temperature;

(G) correcting one of the regional partial pressure value or the systemic partial pressure value for the difference between the body temperature of the subject and the standard temperature so that both the regional partial pressure value and the systemic partial pressure value comprise partial pressure values at a common temperature; and (H) thereafter comparing the regional partial pressure value to the systemic partial pressure value and providing the difference therebetween as a gaseous partial pressure gap measurement.

2. The method according to claim 1 wherein the step of obtaining the systemic gaseous partial pressure value is further defined as obtaining the value from the blood of the subject.

3. The method according to claim 2 wherein the step of obtaining the systemic partial pressure value is further defined as obtaining the value from the arterial blood of the subject.

4. The method according to claim 2 wherein the step of obtaining the systemic partial pressure value is further defined as obtaining the value from the venous blood of the subject.

5. The method according to claim 1 wherein the correcting step is further defined as correcting the body temperature regional partial pressure value to a standard temperature regional partial pressure value.

6. The method according to claim 2 wherein the step of obtaining the systemic partial pressure value from the blood of the subject is further defined as heating the blood of the subject to a standard temperature.

7. The method according to claim 2 wherein the step of obtaining the systemic partial pressure value from the blood of the subject is further defined as altering the systemic partial pressure value obtained from the blood to a standard temperature value.

8. The method according to claim 2 wherein the step of obtaining the systemic partial pressure value from the blood of the subject is further defined as altering the systemic partial pressure value obtained from the blood to a body temperature value.

9. The method according to claim 2 wherein the step of obtaining the systemic partial pressure value is further defined as obtaining the systemic partial pressure value using a blood gas analyzer.

10. The method according to claim 1 wherein the step of obtaining a regional gaseous partial pressure value is further defined as obtaining the regional partial pressure value using an infrared spectrometer.

11. The method according to claim 1 further including the step of measuring the body temperature of the subject and using the measured temperature to carry out the correction of step (G).

12. The method according to claim 8 further including the step of measuring the body temperature of the subject and using the measured temperature to carry out the alteration of the systemic partial pressure value obtained from the blood.

13. The method according to claim 2 wherein the step of obtaining the systemic gaseous partial pressure value is further defined as obtaining a partial pressure value from the end tidal breathing gases of the subject, the end tidal partial pressure value being that for the body temperature of the subject; and wherein the method includes the steps of:

correcting one of the end tidal partial pressure value or the blood partial pressure value for the difference between the body temperature of the subject and the standard temperature if the blood partial pressure value is a standard temperature value so that both the end tidal partial pressure value and the blood partial pressure value comprise partial pressure values at a common temperature;

comparing the end tidal partial pressure value to the blood partial pressure value to determine which of the end tidal partial pressure value or blood partial pressure value is to be utilized as the systemic partial pressure value; and using the selected partial pressure value as the systemic partial pressure value in steps (C) through (H).

14. The method according to claim 13 further including the step of measuring the body temperature of the subject and using the measured temperature to carry out the correction of the end tidal $CO_2$ partial pressure value or blood $CO_2$ partial pressure value.

15. The method according to claim 1 wherein the gaseous partial pressure values are regional and systemic $CO_2$ partial pressure values.

16. The method according to claim 13 wherein the gaseous partial pressure values are regional and systemic $CO_2$ partial pressure values and wherein the partial pressure valve from the end tidal breathing gases is an end $CO_2$ partial pressure valve.

17. The method according to claim 1 wherein the gaseous partial pressure values are regional and systemic $O_2$ partial pressure valves.

18. Apparatus for determining the difference between a regional gaseous partial pressure of a selected body organ of a mammalian subject and a systemic gaseous partial pressure of the subject, the body temperature of the subject being changeable, said apparatus comprising:

a tonometric catheter, the tonometric catheter being placed in contiguity with the selected organ and having a sampling medium for receiving a gaseous component from the organ;

a detector coupled to the tonometric catheter for determining the regional gaseous partial pressure of the organ from the sampling medium, the regional partial pressure value so determined being that for the existing body temperature of the subject;

means for obtaining a systemic gaseous partial pressure value from the blood of the subject at one of a standard temperature or the body temperature of the subject;

means for correcting one of the regional partial pressure value and the systemic partial pressure value for the difference between the body temperature of the subject and the standard temperature when the systemic partial pressure is a standard temperature value so that both the regional partial pressure value and the systemic partial pressure value comprise partial pressure values at a common temperature;

means for comparing the regional partial pressure value and the systemic partial pressure value to determine the difference therebetween; and means for providing an indication of the difference between the regional partial pressure value and the systemic partial pressure value as a gaseous partial pressure gap measurement.

19. The apparatus according to claim 18 wherein said means for obtaining a systemic partial pressure value is further defined as means for obtaining the value from the arterial blood of the subject.

20. The apparatus according to claim 18 wherein said tonometric catheter employs a gaseous sampling medium.

21. The apparatus according to claim 18 wherein said detector comprises an infrared spectrometer.

22. The apparatus according to claim 18 wherein said means for obtaining a systemic partial pressure value from the blood of the subject comprises a blood gas analyzer.

23. The apparatus according to claim 18 further defined as apparatus for determining the difference between a regional $CO_2$ partial pressure and a systemic $CO_2$ partial pressure, wherein the tonometric catheter receives $CO_2$ from the organ, and wherein said obtaining means obtains a systemic $CO_2$ partial pressure valve from the blood of the subject.

24. The apparatus according to claim 23 further including:

means for obtaining an end tidal $CO_2$ partial pressure value from the subject, the end tidal $CO_2$ partial pressure value being that for the body temperature of the subject;

additional correcting means for correcting one of the end tidal $CO_2$ partial pressure value and the blood $CO_2$ partial pressure value for the difference between the body temperature of the subject and the standard temperature when the blood $CO_2$ partial pressure is at the standard temperature so that both the end tidal $CO_2$ partial pressure value and the blood partial pressure value comprise $CO_2$ partial pressure values at a common temperature; and means for comparing the end tidal $CO_2$ partial pressure value to the blood $CO_2$ partial pressure value and for selecting one of said values as the systemic $CO_2$ partial pressure value for supply to said correcting means.

25. The apparatus according to claim 18 further defined as apparatus for determining the difference between a regional $O_2$ partial pressure and a systemic $O_2$ partial pressure, wherein the tonometric catheter receives $O_2$ from the organ, and wherein said obtaining means obtains a systemic $O_2$ partial pressure valve from the blood of the subject.

* * * * *